(12) United States Patent
Mayrose et al.

(10) Patent No.: US 6,752,770 B2
(45) Date of Patent: Jun. 22, 2004

(54) SYSTEM AND METHOD FOR ANALYZING A REGION BELOW ONE OR MORE LAYERS OF TISSUE

(75) Inventors: James Mayrose, Akron, NY (US); Thenkurussi Kesavadas, Amherst, NY (US); Kevin Chugh, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 170 days.

(21) Appl. No.: 09/992,471

(22) Filed: Nov. 14, 2001

(65) Prior Publication Data

US 2002/0133093 A1 Sep. 19, 2002

Related U.S. Application Data

(60) Provisional application No. 60/249,001, filed on Nov. 15, 2000.

(51) Int. Cl.[7] .............................................. A61B 5/103
(52) U.S. Cl. ..................................................... 600/587
(58) Field of Search ................................ 600/587, 561; 73/379.04, 379.05, 379.08, 789, 818

(56) References Cited

U.S. PATENT DOCUMENTS 5,833,633 A * 11/1998 Sarvazyan .................. 600/587
5,836,894 A * 11/1998 Sarvazyan .................. 600/587
5,989,199 A * 11/1999 Cundari et al. ............. 600/587

OTHER PUBLICATIONS

J. Mayrose et al., "A One–Dimensional Approach To Viscoelastic Material Stiffness Calculations," *ASME International Mechanical Engineering Congress and Exposition*, pp. 227–228 (Nov. 15, 1999).
G. C. Burdea, "Force and Touch Feedback for Virtual Reality," John Wiley & Sons, Inc., pp. 186–190 (1996).
J. M. Pereira et al., "The Effects of Layer Properties on Shear Disturbance Propagation in Skin," *Journal of Biomechanical Engineering*, 113:30–35 (1991).
L. S. Friedman, "Diagnosis: Examining the Abdomen," *Hospital Medicine*, pp. 99–116 (1986).

* cited by examiner

*Primary Examiner*—Eric F. Winakur
(74) *Attorney, Agent, or Firm*—Nixon Peabody LLP

(57) ABSTRACT

An apparatus for analyzing a region below one or more layers of tissue includes a force sensor, a position sensor, and a processing system. The force sensor provides a force signal representative of an amount of force applied to a portion of the one or more layers of tissue which is adjacent to the region. The position sensor provides a position signal representative of the location of the position sensor when the force is applied. The processing system coupled to the force sensor and the position sensor determines at least one property of the region based on the force signal and the position signal.

25 Claims, 1 Drawing Sheet

SYSTEM AND METHOD FOR ANALYZING A REGION BELOW ONE OR MORE LAYERS OF TISSUE

This application claims the benefit on U.S. Provisional Patent Application Ser. No. 60/249,001 filed Nov. 15, 2000.

FIELD OF THE INVENTION

This invention relates generally to medical diagnostic and training systems and methods, and more particularly, to a system and method for analyzing a region below one or more layers of tissue.

BACKGROUND OF THE INVENTION

A palpation examination of soft tissue structures is often necessary to obtain an accurate diagnosis for many types of conditions. For example, when treating an abdominal condition, a palpation examination of the abdomen is a critical diagnostic test for determining the appropriate treatment for the condition. These types of palpation examinations provide a wide variety of information, such as the location and intensity of abdominal tenderness, the patient's voluntary and involuntary reactions to abdominal palpation, presence of rebound tenderness, and the size and presence of masses and abdominal organs. The process for diagnosing conditions of the abdomen is described in greater detail in Friedman, L. S., 1986, "Diagnosis: Examining the Abdomen" Hospital Medicine, pp. 99–116 which is herein incorporated by reference in its entirety.

Unfortunately, existing techniques for palpation examinations of soft tissue structures have limitations. One of these limitation is that they provide qualitative, rather than quantitative information about the examined region. As a result, to accurately make a qualitative diagnosis based on a palpation examination requires significant experience. If the individual conducting this type of examination lacks the requisite experience, there may be inaccuracies in the resulting diagnosis. Even with significant experience, the qualitative nature of these types of analyses leaves the opportunity for an error in the diagnosis to occur.

SUMMARY OF THE INVENTION

An apparatus for analyzing a region below one or more layers of tissue in accordance with one embodiment of the present invention includes a force sensor, a position sensor, and a processing system. The force sensor provides a force signal representative of an amount of force applied to a portion of the one or more layers of tissue which is adjacent to the region. The position sensor provides a position signal representative of the location of the position sensor when the force is applied. The processing system coupled to the force sensor and the position sensor determines at least one property of the region based on the force signal and the position signal.

A method for analyzing a region below one or more layers of tissue in accordance with another embodiment of the present invention includes a few steps. Force is applied to a portion of the one or more layers of tissue which is adjacent to the region. The amount of force applied to the portion of the one or more layers of tissue which is adjacent to the region with a force sensor is determined. The location of a position sensor when the force is applied is determined. The position sensor is located adjacent to the force sensor. At least one property of the region is determined based on the amount of force applied to the portion of the one or more layers of tissue which is adjacent to the region and the location of the position sensor.

The present invention provides a viable tool for accurate measurement of physical deviations of viscoelastic materials and can also be used in the modeling of physically based deformable organs. The present invention can be used across many fields of medicine, from emergency abdominal examinations to breast and thyroid examinations, and as an input device for haptic and tactile feedback devices.

More specifically, the present invention allows medical professionals to non-invasively and quantitatively, measure the properties of human tissue, such as the hardness or softness of the tissue. In particular, precise data on the size, location and stiffness of a region being examined can be collected and analyzed. With this collected data, the material properties of various regions of the human body can be determined. This data can be collected without interfering with the physicians sense of touch during a palpation examination which is important for making an accurate diagnosis. Further, the quantitative nature of the data collection reduces the opportunity for an error in diagnosis and reduces the amount of experience required to perform these types of palpation examinations.

DETAILED DESCRIPTION

Figure 1:
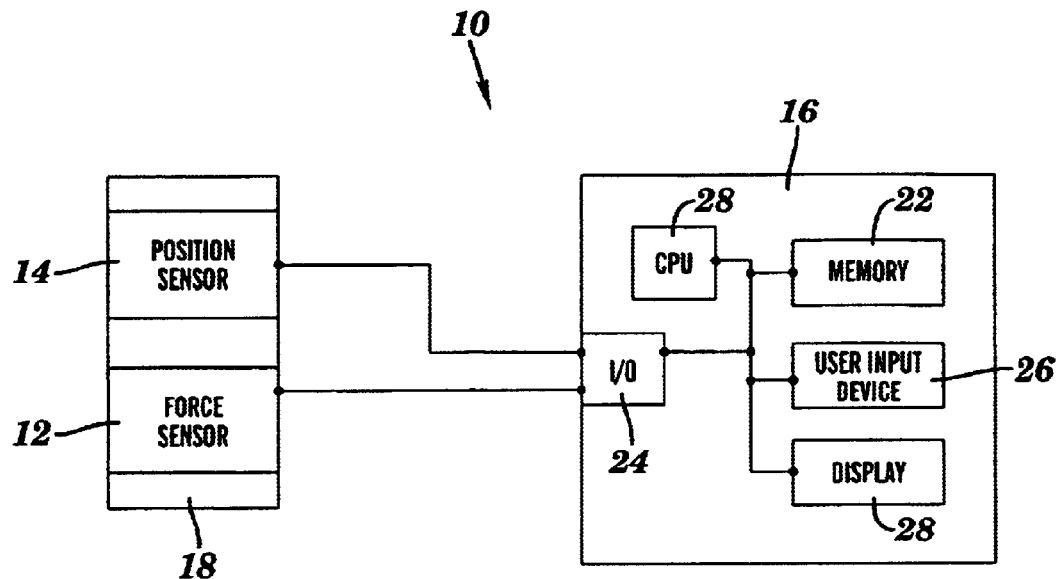
FIG. 1 is a block diagram of a system for analyzing a region below one or more layers of tissue in accordance with one embodiment of the present invention.

A system 10 for analyzing a region below one or more layers of tissue in accordance with one embodiment is illustrated in FIG. 1. The system 10 includes a force sensor 12, a position sensor 14, and a processing system 16. The present invention provides a number of advantages, including an effective and noninvasive system 10 and method for analyzing a region below one or more layers of tissue.

Referring to FIG. 1, the force or pressure sensor 12 is coupled to the processing system 16. The force sensor 12 measures the amount of force or pressure being applied by the individual conducting the palpation examination, such as a physician, to the one or more layers of tissue being examined, such as the layers of skin over the abdominal region. In this particular embodiment, the information about the amount of applied force is transmitted from the force sensor 12 to the processing system 16 at the request of the individual conducting the examination, although this information can be transmitted in other manners, such as continually or periodically. Additionally, in this particular embodiment the force sensor 12 continuously measures the applied force from 0 lbs to 25 lbs at a frequency of 1 H to 200Hz, although the force sensor 12 can measure other applied force ranges at other frequencies.

The force sensor 12 is small enough so that a sensing area of the force sensor 12 can be located on an index finger of the individual conducting the examination, although the force sensor 12 can have other sizes and can be placed in other locations. The small size of the force sensor 12 enables the user to perform examinations of soft tissue areas without interfering with the physicians sense of touch during a palpation examination. By way of example only, a force sensor 12 with a sensing area of about 0.325 inches square, a thickness of about 0.005 inches, and a length of about 9 inches, although again the dimensions of the force sensor 12 can vary as needed. Although one force sensor 12 is shown in this particular embodiment, a plurality or array of force sensors could be used to examine soft tissue with each of the force sensors positioned on a different finger of the operator.

The position sensor 14 is also coupled to the processing system 16 and provides position information on the location of the position sensor 14. In this particular embodiment, the position sensor 14 provides information on the position and orientation of the position sensor 14, although the position sensor 14 can provide other types of position information and this information can be supplied in different manners, such as upon request, periodically, or continually. In this particular embodiment, the position sensor 14 is about 0.35 inches long by 0.24 inches wide and 0.2 inches high, although the dimensions can vary. The small size of the position sensor 14 allows it to be mounted on the fingernail of the individual conducting the palpation examination without hindering the examination. Additionally, in this particular embodiment the position sensor 14 operates at a frequency of 1 Hz to 144 Hz, has a range of thirty inches from the transmitter and is accurate to within 0.07 inches, although these operating parameters can vary based on the particular position sensor 14 used.

An elastic band 18 is connected to the force sensor 12 and the position sensor 14 and is worn over the finger of the user, although other types of support devices to secure the force sensor 12 and position sensor 14 to the operator and other locations for the force sensor 12 and position sensor 14 can be used. In this particular embodiment, wearing the elastic band 18 with the force sensor 12 on the fingerpad and the position sensor 14 on the fingertip allows the user to perform a medical palpation exam without hindering the user's sense of touch.

The processing system 16 is coupled to the force sensor 12 and the position sensor 14 and determines one or more properties of the region being examined based on the information from the force sensor 12 and the position sensor 14. In this particular embodiment, the processing system 16 includes a central processing unit (CPU) or processor 20, a memory 22, an input/output interface 24, a user input device 26, and a display 28 which are coupled together by a bus system 30 or other link, respectively, although the processing system 16 may comprise other components, other numbers of the components, and other combinations of the components.

The processor 20 executes one or more programs of stored instructions for the method for analyzing a region below one or more layers of tissue in accordance with one embodiment of the present invention as described herein. In this particular embodiment, those programmed instructions are stored in one or more memories, such as memory 22 although some or all could be stored and retrieved from other locations. A variety of different types of memory storage devices, such as a random access memory (RAM) or a read only memory (ROM) in the system or a floppy disk, hard disk, CD ROM, or other computer readable medium which is read from and/or written to by a magnetic, optical, or other reading and/or writing system that is coupled to the processor 20, can be used for memory 22.

The input/output interface 24 is used to operatively couple and communicate between the processing system 16 and the pressure and position sensors. A variety of different types of communication methods and protocols can be used for this communication.

The user input device 26 enables an operator to generate and transmit signals or commands to the CPU 20, such as information about the characteristics of the layers above a region to be examined. A variety of different types of user input devices can be used, such as a keyboard or computer mouse.

The display 28 provides a display of the information to the operator, such as information about the properties of the region. A variety of different types of displays can be used such, such as a cathode ray tube display device or a printer.

A method for analyzing a region below one or more layers of tissue in accordance with one embodiment of the present invention will now be described. The elastic band 18 is placed around one of the fingers of the operator. The force sensor 12 is positioned on the fingerpad of the operator and the position sensor 14 is located on the fingernail of the operator. As a result, the force sensor 12 and the position sensor 14 do not substantially interfere with the sense of touch of the individual conducting the palpation examination which is a important for making an accurate diagnosis.

Once the force sensor 12 and the position sensor 14 are in place, the operator will begin the palpation exam of the patient. During the palpation exam, the operator will apply force or pressure against layers of skin of the patient to detect any hard tissue, lumps or other abnormalities. The force sensor 12 and the position sensor 14 will be sending force and position information to the processing system 16. This force and/or position information may be transmitted continually or upon request from the processing system 16.

The processing system 16 receives the force and position information and determines the amount of force currently being applied and the position and orientation of the position sensor. In this particular embodiment, the processing system 16 receives position and orientation signals from the position sensor 14 for an initial position of the position sensor when the force sensor is resting against the portion of the one or more layers of tissue being examined before any amount of force is applied and an engaged position of the position sensor when the amount of force is fully applied, although other position and/or orientation signals could be transmitted and analyzed depending on the particular application. Next, in this particular embodiment the processing system 16 determines a displacement of the one or more layers based on the initial position and the engaged position.

Based on the determined amount of force with a determined displacement, the processing system 16 determines one or more properties of the region being analyzed, such as the stiffness and elasticity of the region. One example of determining the property of stiffness of the region to be examined is set forth in the examples described below, although other methods and/or techniques for determining this and other types of properties can be used by processing system 16.

The present invention enables force and displacement data to be collected during a palpation exam without hindering the physicians sense of touch. With this collected data, which is obtained by non-invasive measurements, the material properties of various regions of the human body can be determined. More specifically, the present invention allows physicians to detect sub-surface tumors and delineate between soft and stiff tissue. The data collected from the present invention can be used to quantify the size, shape, location and stiffness of various sub-surface objects for use in providing a more accurate diagnosis.

To illustrate the present invention, some examples where the method in accordance with one embodiment of the present invention is used for analyzing a region below one or more layers of tissue are set forth below. In these examples, three different densities of polyester foam were used in order to simulate a viscoelastic environment. More specifically, layers of 2 pounds per cubic foot ("pcf") (K=1.052), 4 pcf (K=2.0), and 6 pcf (K=2.22) polyester foam were used to model the various layers 30 and 32 of skin, fat and muscle of the abdomen and HR form (K=2.662), which has a higher stiffness than polyester, to model an organ 34 and was obtained from Par Foam Products Inc., Buffalo, N.Y.

Figure 2:
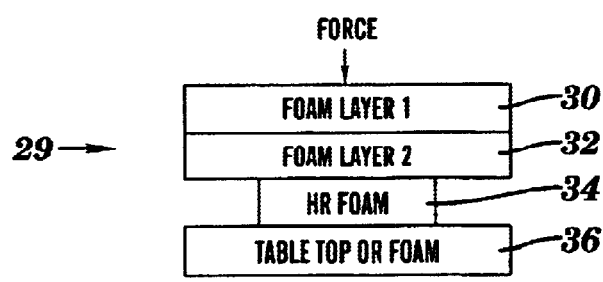
FIG. 2 is a cross-sectional view of a model of layers with a region in the layers to be analyzed.

Referring to FIG. 2, two layers 30 and 32 of one inch foam were placed on top of the one layer 34 of HR foam which is resting on a table top or layer of foam 36. Six different foam configurations for layers 30 and 32 were created and three deformation experiments were conducted with each. A Fakespace pinch glove produced by Mountain View, Calif. with a force sensor 12 produced by Force Imaging Tech., Chicago, Ill. and was located on the fingertip of the middle finger. The force sensor 12 in this particular example is 0.25 inches in diameter and 0.003 inches thick. A "Flock of Birds" (Ascension Technology Corp, Burlington, Vt.) position sensor 14 was placed on the pinch glove on top of the middle finger in order to get an accurate measure of palpation displacement. The experimenter palpated the model 29 three times making contact with the HR foam each time. Force and displacement data were collected for each experiment and use to calculate the stiffness of the HR foam layer 34.

A one-dimensional analytical model was used to calculate the stiffness of the HR foam layer 34. The elements, each of which has its own stiffness constant, combine to give the deformation characteristics of the whole object. In this example, Hooke's law was used to calculate the stiffness of the HR foam 34 as disclosed in Burdea, G. C., 1996, "Force and Touch Feedback for Virtual Reality", John Wiley & Sons, Inc., pp.186–190 which is herein $$x = \sum_{i=1}^{n} \frac{F}{Ki} \quad (1)$$

incorporated by reference in its entirety.

Where F is the force acting upon the object, K is the stiffness constant and x is the total displacement.

Three trials for each of the six experiments were conducted. The average force applied and distance deformed were used in the calculations for each experiment. By utilizing the known stiffness constants of the first two layers 30 and 32 a stiffness constant for the HR foam 34 could be calculated. The results of each experiment are shown in Table 1 below. The known stiffness of HR foam 34 is 2.662 lb/in. The calculated stiffness from experiment numbers 1, 2, 4, and 5 fell within 10% of the actual stiffness of HR foam 34. Experiments 3 and 6 had a calculated stiffness well over 28% of the actual stiffness.

TABLE 1

Experimental Data

| Experiment Number | Layer 1 | Layer 2 | Layer 3 | Layer 4 | Force (lbs) | Displacement (in) | Stiffness (lb/in) |
|---|---|---|---|---|---|---|---|
| 1 | 2 pcf | 4 pcf | HR Foam | Table top | 8.39 | 2.05 | 2.642 |
| 2 | 2 pcf | 6 pcf | HR Foam | Table top | 10.4 | 2.12 | 2.781 |
| 3 | 4 pcf | 6 pcf | HR Foam | Table top | 17.4 | 2.19 | 3.425 |
| 4 | 2 pcf | 4 pcf | HR Foam | 2 pcf | 15.5 | 2.52 | 2.436 |
| 5 | 2 pcf | 6 pcf | HR Foam | 2 pcf | 16.8 | 2.77 | 2.665 |
| 6 | 4 pcf | 6 pcf | HR Foam | 2 pcf | 25.2 | 3.29 | 3.444 |

In these experiments in the table above, layer 1 corresponds to layer 30, layer 2 corresponds to layer 32, layer 3 corresponds to layer 34, layer 4 corresponds to layer 36. Experiments 1 and 4 were paired as were experiments 2 and 5 and experiments 3 and 6, the only difference being the material used for the fourth layer 36. The calculated values of stiffness in experiments 1, 2, 4 and 5 correlated well with the actual value. The immeasurable deformation of the fourth layer 36 in experiments 4 and 5, which was a two inch piece of 2 pcf foam, did not have a significant effect on the calculated stiffness coefficient. A greater force had to be applied in these experiments, which in turn caused a greater deformation in order to actually feel the HR foam 34 beneath the surface of layers 30 and 32. The poor results achieved in experiments 3 and 6 were due in part to the large stiffness constants of the first two layers 30 and 32 of foam. Large forces had to be applied in order to penetrate the outer layers 30 and 32 of foam in order to feel the HR foam beneath the surface. These poor results are not a concern because the forces applied are well beyond the range of forces that would normally occur or be required during a routine abdominal examination.

These examples assume that the stiffness of both layers 30 and 32 are known. When the present invention is used to calculate the stiffness constants of real human tissue, muscles and organs, the properties of the layers of skin and other layers of tissue will need to be determined or may be obtained in other manners, such as from Pereira, J. M., Mansour, J. M., 1991, "The Effects of Layer Properties on Shear Disturbance Propagation in Skin", Journal of Biomedical Engineering, Vol. 113, pp. 30–35 which is herein incorporated by reference in its entirety. If the stiffness of each layer 30 and 32 of soft tissue and muscle is not known, it will need to be calculated before the stiffness of the organ 34 can be determined.

The data presented in this study shows that the present invention is a viable tool for accurate measurement of physical deviations of viscoelastic materials. The present invention can also be used in the modeling of physically based deformable organs.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Accordingly, the invention is limited only by the following claims and equivalents thereto.

What is claimed is:

1. An apparatus for analyzing a region below one or more layers of tissue, the apparatus comprising:
   a force sensor that provides a force signal representative of an amount of force applied to a portion of the one or more layers of tissue which is adjacent to the region;
   a position sensor that provides a position signal representative of the location of the position sensor when the force is applied;
   a support device that attaches the force sensor and the position sensor to an extremity of an operator; and
   a processing system coupled to the force sensor and the position sensor that determines at least one property of the region based on the force signal and the position signal.

2. The apparatus as set forth in claim 1 wherein the support device is an elastic band that fits around a finger of the operator.

3. The apparatus as set forth in claim 1 wherein the position sensor provides an orientation signal representative of the orientation of the position sensor when the force is applied, wherein the processing system uses the orientation signal to determine the at least one property of the region.

4. The apparatus as set forth in claim 1 further comprising two or more of the force sensors and two or more of the position sensors, wherein the processing system uses the position signals and the force signals from each of the two or more force sensors and each of the two or more position sensors to determine the at least one property of the region.

5. An apparatus for analyzing a region below one or more layers of tissue, the apparatus comprising:
   a force sensor that provides a force signal representative of an amount of force applied to a portion of the one or more layers of tissue which is adjacent to the region;
   a position sensor that provides a position signal representative of the location of the position sensor when the force is applied; and
   a processing system coupled to the force sensor and the position sensor that determines a displacement of the one or more layers based on the position signal and determines at least one property of the region based on the force signal, the position signal, and the displacement.

6. The apparatus as set forth in claim 5 wherein the position signal comprises an initial position signal representative of the location of the position sensor when the force sensor is resting against the portion of the one or more layers of tissue which is adjacent to the region before the amount of force is applied and an engaged position signal representative of the location of the position sensor when the amount of force is applied, wherein the processing system determines the displacement based on the initial position signal and the engaged position signal.

7. An apparatus for analyzing a region below one or more layers of tissue, the apparatus comprising:
   a force sensor that provides a force signal representative of an amount of force applied to a portion of the one or more layers of tissue which is adjacent to the region;
   a position sensor that provides a position signal representative of the location of the position sensor when the force is applied; and
   a processing system coupled to the force sensor and the position sensor that determines at least one property of the region based on the force signal and the position signal, wherein the at least one property is a stiffness constant.

8. A method for analyzing a region below one or more layers of tissue, the method comprising:
   applying force to a portion of the one or more layers of tissue which is adjacent to the region;
   determining an amount of force applied to the portion of the one or more layers of tissue which is adjacent to the region with a force sensor;
   determining a location of a position sensor when the force is applied, the position sensor is adjacent to the force sensor;
   attaching the force sensor and the position sensor to an extremity of an operator; and
   determining at least one property of the region based on the amount of force applied to the portion of the one or more layers of tissue which is adjacent to the region and the location of the position sensor.

9. The method as set forth in claim 8 wherein attaching further comprises:
   attaching the force sensor to a fingerpad portion of a finger of the operator; and
   attaching the position sensor adjacent to the fingerpad portion.

10. The method as set forth in claim 8, further comprising determining an orientation of the position sensor when the force is applied, wherein the orientation is used in the determining of the at least one property of the region.

11. The method as set forth in claim 8 further comprising:
    determining two or more amounts of force applied to the portion of the one or more layers of tissue which is adjacent to the region with two or more of the force sensors; and
    determining a location of each of the force sensors when the amounts of force are applied using two or more of the position sensors, each of the position sensors is adjacent to one of the force sensors; and
    wherein the determined amounts of force applied to the portion of the one or more layers of tissue which is adjacent to the region and the determined locations of the position sensors are used in the determining the at least one property of the region.

12. A method for analyzing a region below one or more layers of tissue, the method comprising:
    applying force to a portion of the one or more layers of tissue which is adjacent to the region;
    determining an amount of force applied to the portion of the one or more layers of tissue which is adjacent to the region with a force sensor;
    determining a location of a position sensor when the force is applied, the position sensor is adjacent to the force sensor wherein the determining a location of the position sensor when the force is applied further comprises determining a displacement of the one or more layers based on the position signal; and
    determining at least one property of the region based on the amount of force applied to the portion of the one or more layers of tissue which is adjacent to the region, the location of the position sensor, and the displacement.

13. The method as set forth in claim 12 wherein the determining a displacement based on the position signal further comprises:
    determining an initial position of the position sensor when the force sensor is resting against the portion of the one or more layers of tissue which is adjacent to the region before the amount of force is applied;

determining an engaged position of the position sensor when the amount of force is applied; and determining the displacement of the one or more layers based on the initial position and the engaged position.

14. A method for analyzing a region below one or more layers of tissue, the method comprising:

applying force to a portion of the one or more layers of tissue which is adjacent to the region;

determining an amount of force applied to the portion of the one or more layers of tissue which is adjacent to the region with a force sensor;

determining a location of a position sensor when the force is applied, the position sensor is adjacent to the force sensor; and determining at least one property of the region based on the amount of force applied to the portion of the one or more layers of tissue which is adjacent to the region and the location of the position sensor, wherein the at least one property is a stiffness constant.

15. An apparatus for analyzing a region below one or more layers of tissue, the apparatus comprising:

a glove with a plurality of digits;

a plurality force sensors, each of the force sensors is connected to one of the digits of the glove and provides a force signal representative of an amount of force applied to a portion of the one or more layers of tissue which is adjacent to the region;

a plurality of position sensors, each of the position sensors is connected to one of the digits of the glove and adjacent one of the force sensors, each of the position sensors provides a position signal representative of the location of the position sensor when the force is applied; and a processing system coupled to the force sensors and the position sensors that determines at least one property of the region based on the force signals and the position signals.

16. The apparatus as set forth in claim 15 wherein each of the position sensors provide an orientation signal representative of the orientation of the position sensor when the force is applied, wherein the processing system uses the orientation signals to determine the at least one property of the region.

17. The apparatus as set forth in claim 15 wherein the processing system determines displacements of the one or more layers based on the position signals, the processing system using the displacements to determine the at least one property of the region.

18. The apparatus as set forth in claim 17 wherein each of the position signals from each of the position sensors comprises an initial position signal representative of the location of one of the position sensors when the force sensor adjacent the position sensor is resting against the portion of the one or more layers of tissue before the amount of force is applied and an engaged position signal representative of the location of the one of the position sensors when the amount of force is applied, wherein the processing system determines the displacements based on the initial position signals and the engaged position signals.

19. The apparatus as set forth in claim 11 wherein the at least one property is a stiffness constant.

20. A method for analyzing a region below one or more layers of tissue with digits of a hand, the method comprising:

applying forces to a portion of the one or more layers of tissue which is adjacent to the region with two or more of the digits of the hand;

determining an amount of the force applied by each of the digits;

determining a displacement of the one or more layers of tissue by each of the digits; and determining at least one property of the region based on the determined two or more amounts of force and determined displacements.

21. The method as set forth in claim 19 further comprising determining an orientation of each of the digits when the force is applied, wherein the orientation is used in the determining of the at least one property of the region.

22. The method as set forth in claim 19 wherein the determining a displacement further comprises:

determining an initial position of each of the digits resting against the portion of the one or more layers of tissue which is adjacent to the region before the forces are applied;

determining an engaged position of each of the digits when the amount of force is applied; and determining the displacements of the one or more layers for each of the digits based on the initial positions and the engaged positions.

23. The method as set forth in claim 20 wherein the at least one property is a stiffness constant.

24. An apparatus for analyzing a region below one or more layers of tissue, the apparatus comprising:

a force sensor that provides a force signal representative of an amount of force applied to a portion of the one or more layers of tissue which is adjacent to the region;

a position sensor that provides a position signal representative of the location of the position sensor when the force is applied; and a processing system coupled to the force sensor and the position sensor that determines at least one property of the region adjacent to the one or more layers of tissue, based on the force signal, the position signal, and the known properties of the one or more layers of tissue.

25. A method for analyzing a region below one or more layers of tissue, the method comprising:

applying force to a portion of the one or more layers of tissue which is adjacent to the region;

determining an amount of force applied to the portion of the one or more layers of tissue which is adjacent to the region with a force sensor;

determining a location of a position sensor when the force is applied, the position sensor is adjacent to the force sensor; and determining at least one property of the region based on the amount of force applied to the portion of the one or more layers of tissue which is adjacent to the region, the location of the position sensor, and the known properties of the one or more layers of tissue.

* * * * *